(12) United States Patent
Passaglia et al.

(10) Patent No.: US 10,758,408 B1
(45) Date of Patent: Sep. 1, 2020

(54) TETHERED EYE CANNULA AND METHOD OF USE

(71) Applicants: Christopher Lawrence Passaglia, Lutz, FL (US); Sharad Suryakant Malavade, Brandon, FL (US)

(72) Inventors: Christopher Lawrence Passaglia, Lutz, FL (US); Sharad Suryakant Malavade, Brandon, FL (US)

(73) Assignee: University of South Florida, Tampa, FL (US)

( * ) Notice: Subject to any disclaimer, the term of this patent is extended or adjusted under 35 U.S.C. 154(b) by 245 days.

(21) Appl. No.: 15/783,458

(22) Filed: Oct. 13, 2017

Related U.S. Application Data

(60) Provisional application No. 62/407,825, filed on Oct. 13, 2016.

(51) Int. Cl.
| | | |
|---|---|---|
| *A61F 9/00* | (2006.01) | |
| *A61B 3/16* | (2006.01) | |
| *A61B 17/34* | (2006.01) | |

(52) U.S. Cl.
CPC .............. *A61F 9/0017* (2013.01); *A61B 3/16* (2013.01); *A61B 17/34* (2013.01); *A61B 2017/3458* (2013.01); *A61B 2017/3482* (2013.01)

(58) Field of Classification Search
CPC ......... A61F 9/0017; A61B 3/16; A61B 17/34; A61B 2017/3458; A61B 2017/3482
See application file for complete search history.

(56) References Cited

U.S. PATENT DOCUMENTS

| | | | | |
|---|---|---|---|---|
| 2005/0273033 | A1* | 12/2005 | Grahn | A61F 9/00781 604/9 |
| 2011/0196487 | A1* | 8/2011 | Badawi | A61F 9/00781 623/4.1 |
| 2016/0038338 | A1* | 2/2016 | Rangel-Friedman | A61F 9/0017 606/107 |
| 2016/0302965 | A1* | 10/2016 | Erickson | A61F 9/0017 |

OTHER PUBLICATIONS

Downs et al., 24-Hour IOP Telemetry in the Nonhuman Primate: Implant System Performance and Initial Characterization of IOP at Multiple Timescales, IOVS, Sep. 2011, vol. 52, No. 10, pp. 7365-7375.
McLaren et al., Continuous Measurement of Intraocular Pressure in Rabbits by Telemetry, Investigative Ophthalmology & Visual Science, May 1996, vol. 37, No. 6, pp. 966-975.

* cited by examiner

*Primary Examiner* — Kathleen S Holwerda
*Assistant Examiner* — Brooke LaBranche
(74) *Attorney, Agent, or Firm* — Nicholas Pfeifer; Smith & Hopen, P.A.

(57) ABSTRACT

A tethered cannula having at least two curved sections for implantation into an eye and a method for implanting the cannula in the eye. The cannula can withstand ever present and changing rotational forces from eye movement and mechanical forces from the movement of the subject. The cannula can be connected to implantable or tetherable devices that are too large, heavy, or obstructive to attach directly to the eye, such as an intraocular pressure sensor or infusion pump.

13 Claims, 6 Drawing Sheets
(4 of 6 Drawing Sheet(s) Filed in Color)

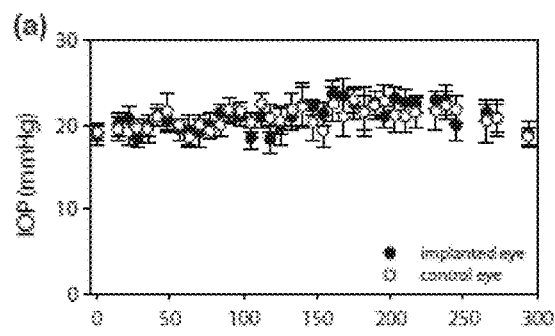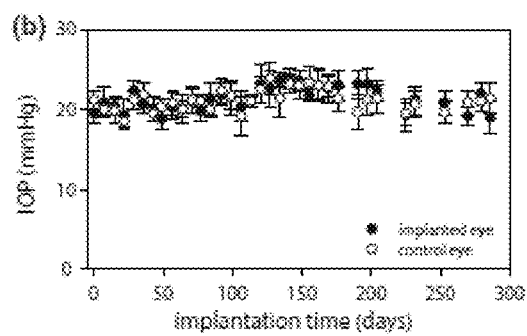
Fig. 6 A
Fig. 6 B
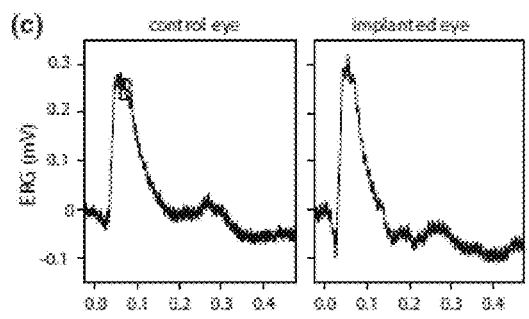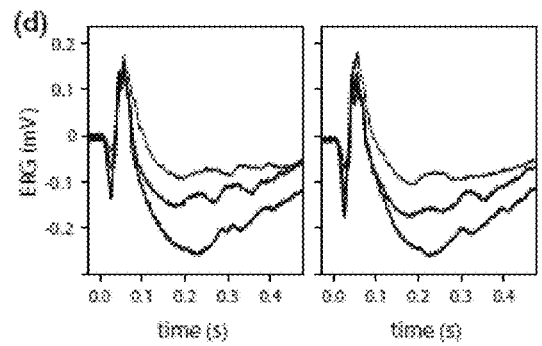
Fig. 6 C
Fig. 6 D

TETHERED EYE CANNULA AND METHOD OF USE

CROSS-REFERENCE TO RELATED APPLICATIONS

This nonprovisional application is a continuation of and claims priority to provisional application No. 62/407,825, entitled "METHOD OF IMPLANTING A TETHERED CANNULA IN THE EYE," filed Oct. 13, 2016 by the same inventors.

FEDERALLY SPONSORED RESEARCH OR DEVELOPMENT

This invention was made with Government support under Grant No. R21EY023376 awarded by the National Institutes of Health. The government has certain rights in the invention.

BACKGROUND OF THE INVENTION

1. Field of the Invention

This invention relates, generally, to cannulas. More specifically, it relates to a novel eye cannula shape and a method of implanting and securing a tethered cannula to the eye.

2. Brief Description of the Prior Art

The treatment of eyes is typically a difficult medical task. Ophthalmic drugs instilled in the eye are usually diluted by tears and cleared by tear ducts, and only a small fraction actually reaches the targeted tissues inside the eye. Intraocular fluid spaces on the other hand are difficult to access. A fine gauge needle can be inserted for a short duration, but needles are not a viable option when long-term access is desired.

There are currently two techniques that disclose a cannula, connected to an external device (pressure sensor in this case), implanted in the anterior chamber of the eye of a conscious animal [1,2]. The first study used a straight cannula and multi-loop suturing technique in rabbits. See McLaren J W, Brubaker R F, and Fitzsimon J S 1996, *Continuous measurement of intraocular pressure in rabbits by telemetry. Invest. Ophthalmol.* Vis. Sci. 37 966-975. This approach is prone to cannula slippage from animal movement. The second study used a straight cannula and a "scleral tube anchor plate" to secure the cannula to the eyes of monkeys. See Downs J C et al 2011, *24-hour IOP telemetry in the nonhuman primate: implant system performance and initial characterization of IOP at multiple timescales. Invest. Ophthalmol.* Vis. Sci. 52 7365-7375. The technique disclosed therein used a non-bent cannula and required an additional "scleral anchor plate," which may not work as well in animals with smaller eyes like rats.

Tethered eye cannulas impose additional mechanical forces that can cause the inserted end of the cannula to move within the eye causing damage to the eye. This issue stems from the fact that a tethered cannula is secured at a second end and no longer able to simply move with the eye. Thus, eye, head, and body movements can tug on the cannula and pull it out, push it further in the eye, or causes it to move sideways within the eye. A straight tethered cannula does not work very well due to this issue. It eventually rotates, slips in, or slips out, all of which have a negative impact on the subject.

Accordingly, what is needed is a tethered eye cannula that can be secured to the eye without being susceptible to forces created from the tethered nature of the cannula and a method of implanting said cannula to ensure that the device remains insusceptible to mechanical forces that could reorient or eject the device. However, in view of the art considered as a whole at the time the present invention was made, it was not obvious to those of ordinary skill in the field of this invention how the shortcomings of the prior art could be overcome.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for a tethered eye cannula and a method of implanting said cannula such that it can be secured to the eye without being susceptible to forces created from the tethered nature of the cannula is now met by a new, useful, and nonobvious invention.

The novel structure includes a first end and a second end with a body extending therebetween. The body is hollow with a first opening at the first end of the cannula and a second opening at the second end of the cannula to permit fluid to flow into and out of the body of the cannula. In moving from the first end of the cannula to the second end of the cannula, the body has a first curve proximate the first end of the cannula followed by a second curve. The first curve can be thought of as being concave, while the second curve is convex. In other words, the open sides of the curves face generally away from each other rather than being in the same direction and effectively creating a circle or semicircle.

In an embodiment, the first and second curves in the body collectively appear to be generally Z-shaped. An embodiment may also include the first curve and the second curve each having an angle less than 90-degrees. Furthermore, an embodiment includes the first and the second curves residing generally in a plane, wherein the plane, when viewed along the edge of the plane, is arced in a lateral direction, i.e. a direction generally perpendicular to the plane. The degree of the curvature roughly matches the degree of curvature of an eye on which the cannula is intended to be attached. In other words, the first and second curves are collectively also arced in the same lateral direction to a degree roughly equal to the curvature of a subject's eye.

An embodiment may also include the second end of the cannula tethered to a medical device. An embodiment includes the cannula being comprised entirely of a biocompatible material.

The novel method of implanting a cannula into an eye includes pre-shaping a cannula to include two consecutive bends, wherein a first bends opens in a first direction and a second bend opens in a second direction, such that a shape of the two consecutive bends and an intermediate section between the bends is representative of a Z-shape. The novel method further includes cutting an incision in a subject's eye; threading an insertion portion of the cannula at the first end of the cannula into the subject's eye through the incision; securing the cannula to the subject's eye by suturing at least the first bend, the intermediate section, and the second bend to the subject's eye; and connecting the second end of the cannula to a medical device.

An embodiment also includes the step of curving an attachment portion of the cannula, which includes the first bend, the intermediate section, and the second bend, to roughly match a degree of curvature of the subject's eye, wherein the curvature of the attachment portion of the cannula is generally perpendicular to an extent of the attachment portion.

In an embodiment, the step of pre-shaping the cannula further comprises shaping the first curve and the second curve such that each has an angle less than 90-degrees.

An embodiment also includes the step of dissecting conjunctival tissue to provide surgical space for attaching the cannula to the sclera in the subject's eye and the step of connecting the cannula to a subdermal coupler that is anchored to bone.

An object of the invention is to provide a novel cannula design and method of implanting said cannula to reduce forces experienced on the insertion portion of the cannula when the cannula is tethered to a medical device.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a fuller understanding of the invention, reference should be made to the following detailed description, taken in connection with the accompanying drawings, in which:

FIG. 6A is a graph of TOP history of implanted rat eyes. Each data point is the average of six tonometer readings and bars are standard deviation.

FIG. 6B is a graph of TOP history of implanted rat eyes. Each data point is the average of six tonometer readings and bars are standard deviation.

FIG. 6C is a graph of Flash ERG records of implanted and non-implanted eyes of two rats after six weeks. Each record is the average of thirty responses to full-field flashes with an interstimulus interval of three seconds. Flash intensity was 4.3 (thin trace), 8.6 (thicker trace), and 17.2 kcd/m$^2$ (thickest trace).

FIG. 6D is a graph of Flash ERG records of implanted and non-implanted eyes of two rats after six weeks. Each record is the average of thirty responses to full-field flashes with an interstimulus interval of three seconds. Flash intensity was 4.3 (thin trace), 8.6 (thicker trace), and 17.2 kcd/m$^2$ (thickest trace).

DETAILED DESCRIPTION OF THE INVENTION

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

The invention addresses the problem of securing a tethered cannula within a subject's eye without the risk of the insertion portion of the cannula or the cannula tip inside the eye moving after being implanted. A cannula may be tethered to a device, such as a pressure measuring device or a fluid adjustment device, that is secured on or to the subject. A tethered cannula, in particular, is more susceptible to movement/dislodgement while implanted because the forces experienced by the cannula are constantly changing as the subject and the subject's eye move. A minor change in a cannula's position could cause dislodgment from the eye or serious injury to internal ocular tissues. The present invention cures this problem.

The present invention includes a novel cannula and method for implanting and tethering the novel cannula. The cannula can be implanted and withstand ever present and changing rotational forces from eye movements and tugging forces from body movement. The cannula can be connected to implantable or tetherable devices that are too large, heavy, or obstructive to attach directly to the eye, such as an intraocular pressure sensor or an infusion pump. Moreover, the novel device allows for chronic movement of agents into or out of the eye and for chronic changes of pressure within the eye of a conscious and functioning subject. The present invention provides researchers and clinicians a robust, reliable, and effective means of chronically assessing intraocular fluid spaces without damaging the eye.

Due to the intended function of the cannula, it is comprised of a biocompatible material enabling it to remain implanted in an eye with minimal complications associated with the material. In addition, the cannula is preferably flexible or shaped to eye curvature to avoid misshaping the eye when the cannula is secured to the outer surface of the eye, the sclera, or another part of the eye.

Moreover, the cannula is tubular to allow for the flow of fluids into or out of a subject's eye when implanted. Furthermore, the cannula has an outer diameter sized to fit within the anterior chamber, posterior chamber, or vitreous chamber of an eye in which the cannula is being implanted.

Figure 1A:
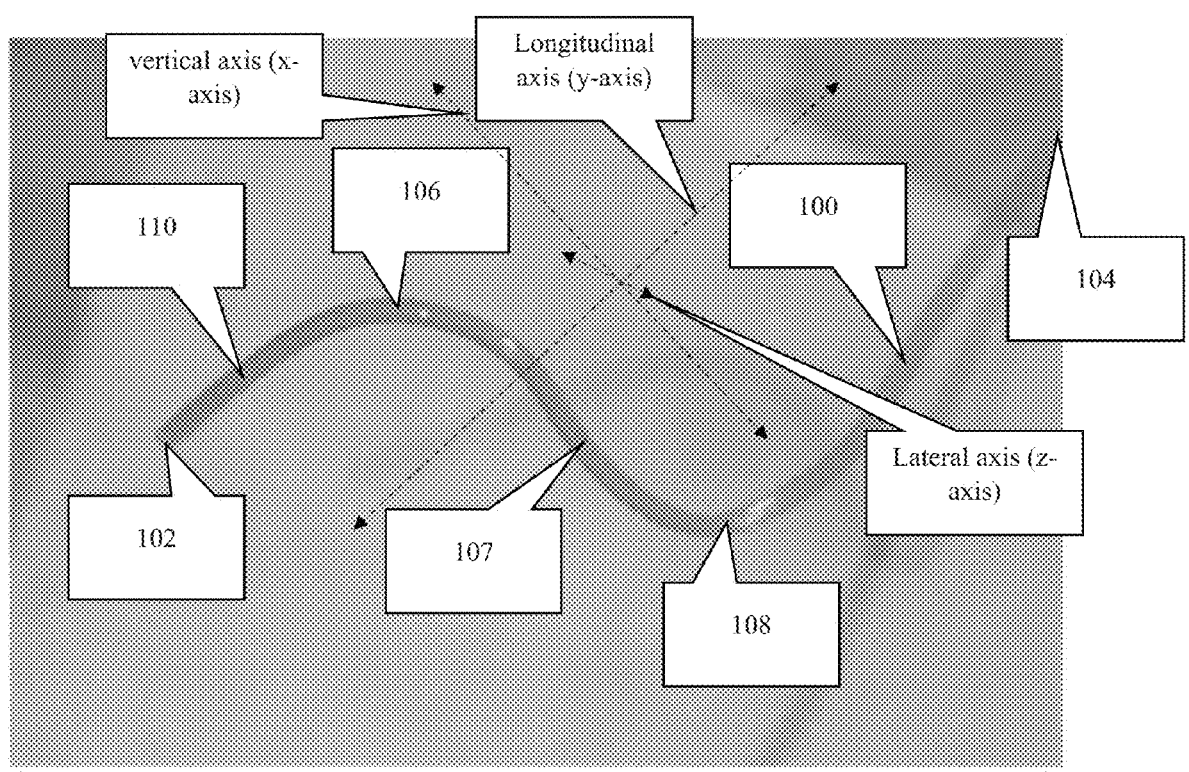
FIG. 1A is a first perspective view of an embodiment of the present invention.
Figure 1B:
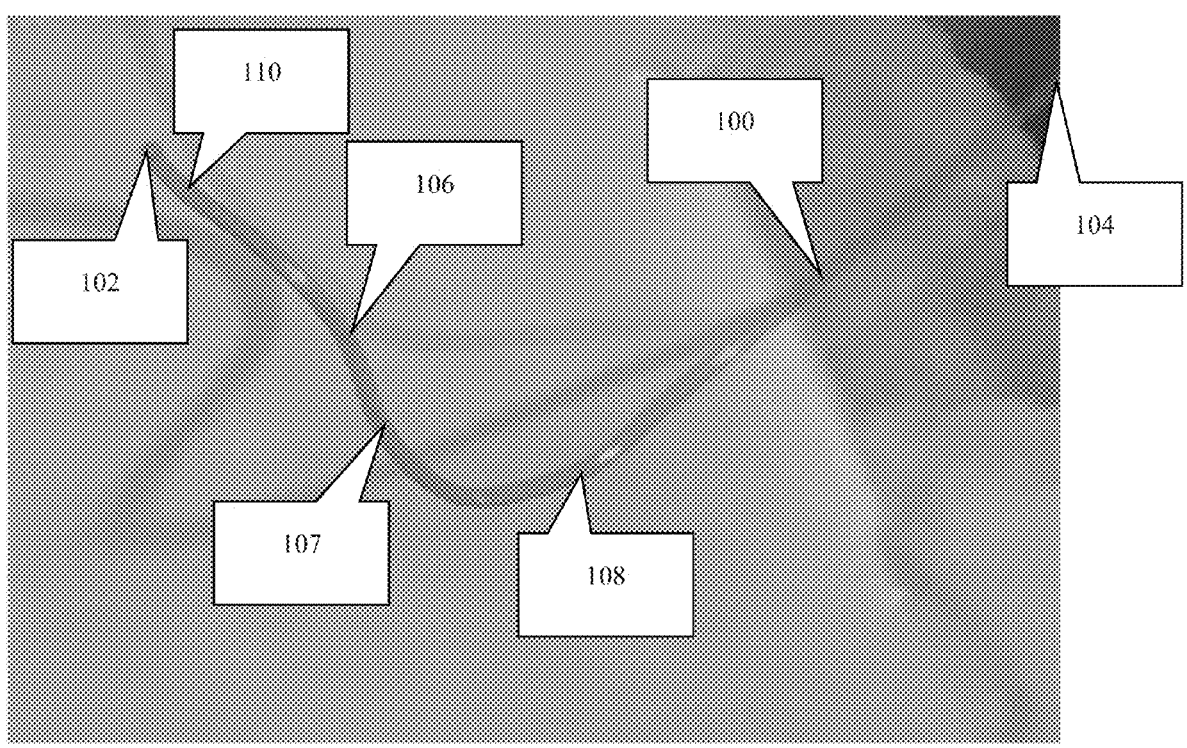
FIG. 1B is a second perspective view of the device shown in FIG. 1B, wherein this view includes the cannula rotated about the longitudinal axis of the cannula. The longitudinal axis is in the general direction of the overall length of the cannula.
Figure 1C:
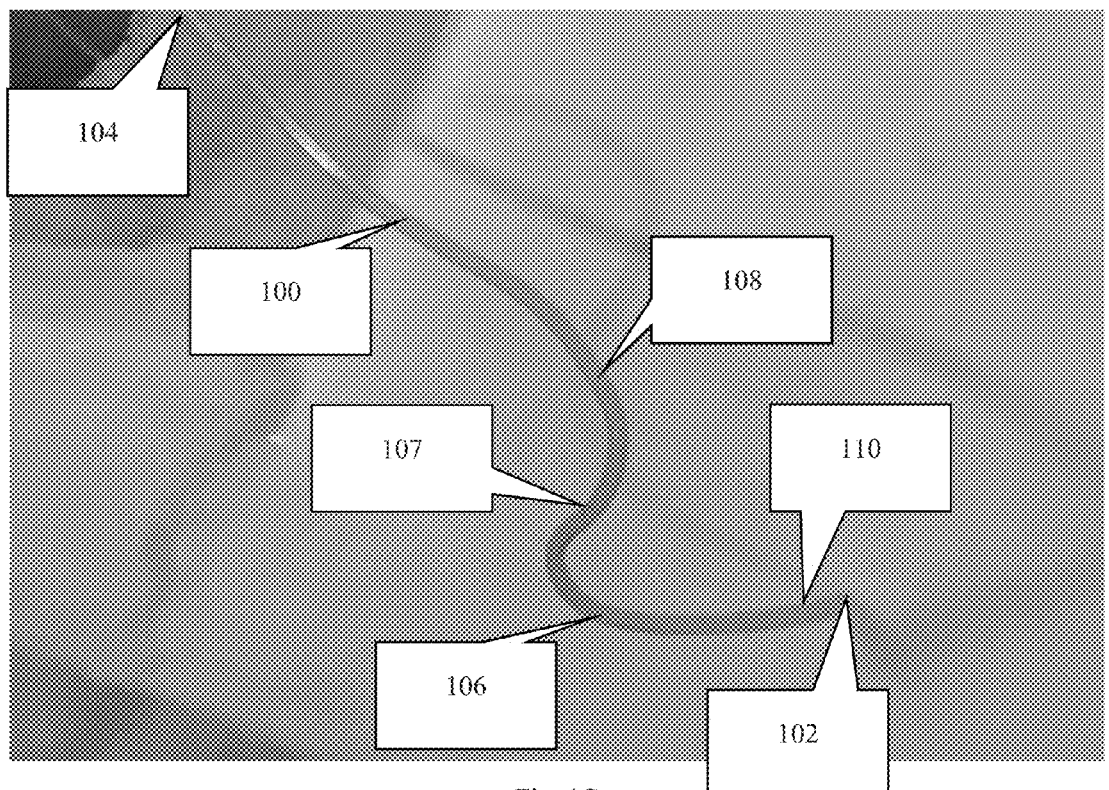
FIG. 1C is a perspective view of an embodiment of the cannula.

As depicted in FIGS. 1-2, the novel cannula, generally denoted by reference numeral 100, includes first end 102, second end 104, and a body extending therebetween. In moving from first end 102 to second end 104, cannula 100 includes an insertion section 110 followed by first curved section 106, an intermediate (usually diagonal) section 107, and curved section 108. The insertion section 110 is typically a straight section, but may have a specific shape or curve depending on where the insertion section is intended to reside within the eye.

Following insertion section 110, cannula 100 includes several bends or curves 106, 108 such that cannula 100 has a shape representative of a Z when viewed from what can be considered a profile view or a lateral, side view. Curves 106, 108 following insertion section 110 are important for providing anchoring points to secure the cannula. A straight shape easily slides out of the eye when tugging forces are applied to the cannula, such as from eye movements. Curves 106, 108, however, absorb and dissipate forces from the tethering before said forces reach insertion portion 110 of cannula 100. In other words, the curves and the suturing of said curves to the eye (often the sclera) prevent insertion section 110 from moving relative to the eye when the subject moves its eye or body.

An embodiment of cannula 100 may include additional curves between insertion portion 110 and second end 104. In an embodiment, each curve 106, 108 creates an acute angle (i.e. less than 90 degrees) with the portions of the cannula just fore and aft of the curve. With oblique angles, the intermediate area 107 between curves has a diagonal orientation. An embodiment may include each curve/bend/arc having a center point/radius point (the point used to determine the radius of the curve) that resides on either the first side of the cannula or the second side of the cannula. Consecutive curves, disregarding intermediate sections, include center points on opposite sides of the cannula. To explain further, if the middle point between the first and second curves is the point at which the cannula is divided into a first side and a second side (first side is the side corresponding to the first end and the second side is the side corresponding to the second end) then the center point/radius points of consecutive curves must be on opposite sides of said middle point between the first and second curves. For example, the first curve has a center point on the first side of the cannula and the second curve has a center point on the second side of the cannula. This orientation ensures that two consecutive curves do not create a circle or semicircle.

Figures 2A, 2B:
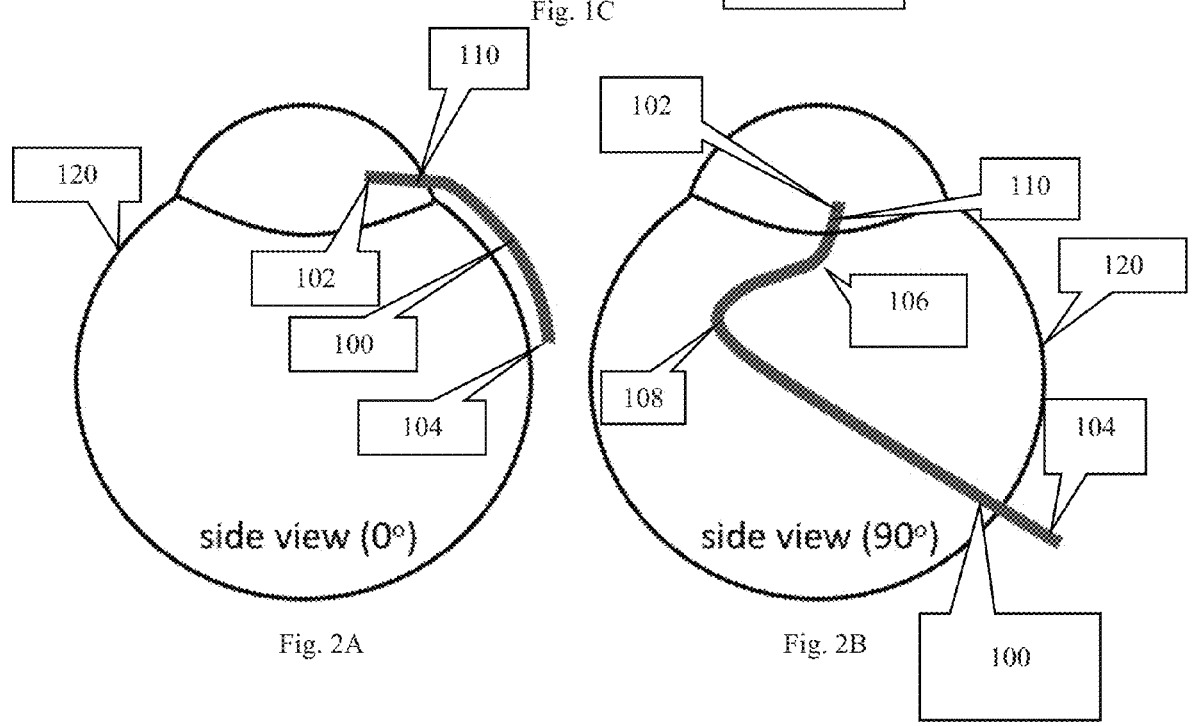
FIG. 2A depicts the cannula inserted into a portion of an eye to show the lateral curve of the attachment section of the cannula.
FIG. 2B depicts the cannula inserted into a portion of an eye with the eye being rotated 90 degrees about a central viewing axis to show the first and second curves of the cannula.

The portion of the cannula intended to be secured to the eye of the subject (referred to as the attachment section), which includes curved sections 106, 108 and the intermediate section 107, is curved in a lateral direction to match the curvature of the subject's eye. To clarify the direction of the curvature, attachment section, i.e. sections 106-108, can be thought of as residing within the same x-y plane. This x-y plane if viewed from a direction in line with the y-axis, would have a curved/arched shape, which is shown in FIG. 2A. As shown, the degree of arc or curvature is dependent on the curvature of the eye on which the cannula will be secured.

Figure 3:
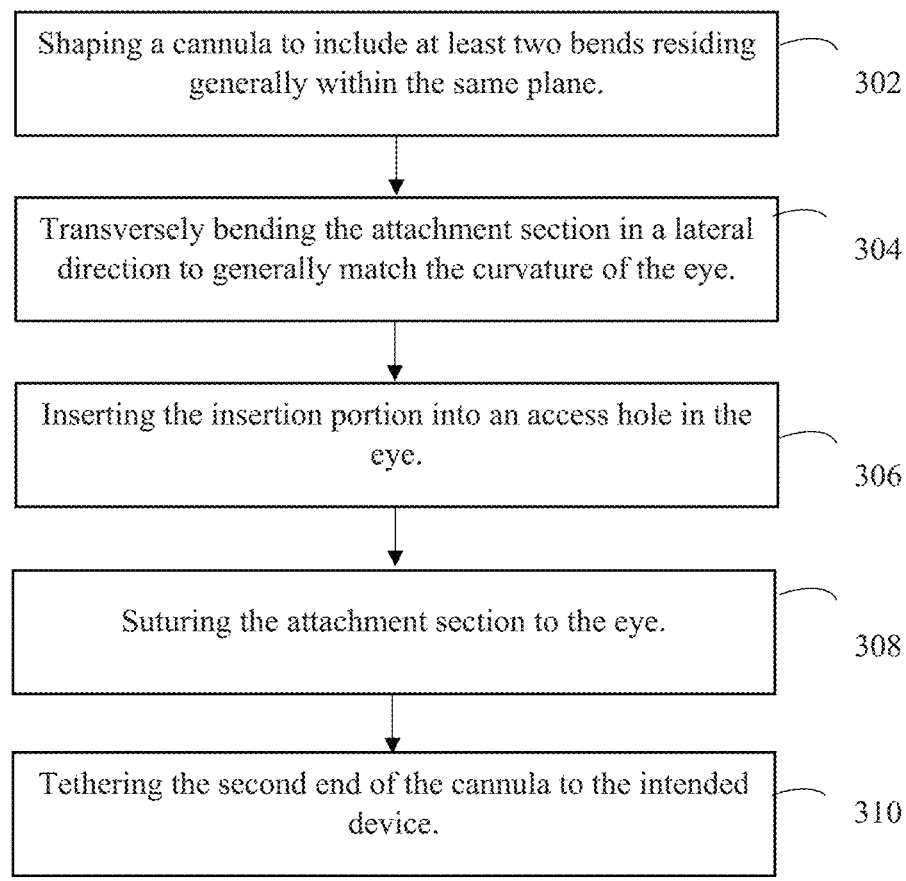
FIG. 3 is an embodiment of the novel method of the present invention.

An embodiment of the novel method, as depicted in FIG. 3, includes shaping the cannula into generally a Z-shape (or a shape having at least two curves/bends) at step 302 and then transversely/laterally bending the curved sections, i.e. attachment section, in a direction perpendicular to a hypothetical plane in which the attachment section resides, at step 304. The transversal/lateral curve is shaped to generally match the curvature of the eye on which the cannula is intended to be sutured. This can be accomplished by creating a custom mold or by bending a hypodermic needle (23G for rat eyes) into the desired shape. The cannula is threaded through the curved needle and permanently re-shaped by applying heat to bends in the needle.

At step 306 the insertion section of the cannula is inserted into an access hole within the subject's eye. Then at step 308, at least three sutures are used to secure the cannula to the subject's eye. There is preferably at least one suture secured at the first curve 106, at least one suture secured at a point along the intermediate section 107, and at least one suture secured at the second curved section 108. These suture locations help reduce the forces experienced by the insertion section. More sutures may be used to further reduce the forces experienced by the insertion section.

Once the cannula is secured to the eye, the second end of the cannula can be tethered to the device. The relative timing of the tethering could occur at other points during the procedure.

An embodiment of the method further includes aestheticizing the subject and applying fluid to contract the iris of the eye prior to creating an incision for the access hole. The eyelid is then retracted, and an incision is made in the conjunctiva parallel to the limbus near the nasal canthus. The canthus location is important for avoiding muscles of the eye and eyelid, which would pull on the cannula and cause dislodgement. A hole can alternatively be tunneled into the posterior chamber or vitreous chamber with the hypodermic needle and the cannula tip placed in those compartments if desired.

Conjunctival tissue is then dissected anteriorly to provide surgical space for cannula attachment to the sclera. The cannula is filled with sterile artificial aqueous humor or physiological saline and threaded into a hypodermic needle (23G for rat eyes), which is slid along the sclera through the incision to the medial orbital wall, where it is redirected vertically to the scalp. The needle is removed, and, in an embodiment, the cannula is connected to a subdermal coupler that is anchored to bone with screws and/or bone cement. The coupler feeds the cannula to the external tether system through which agents can be delivered or intraocular pressure can be measured. More importantly, the coupler isolates the cannula from tugging forces caused by movements of the subject.

If necessary, the insertion section of the cannula is further shaped to the curvature of the iridocorneal angle. When the insertion section is intended to reside within the anterior chamber, a hole is tunneled into the anterior chamber with a hypodermic needle (33G for rat eyes) directed under the circumlimbal venous plexus and angled at 30 degrees to avoid iris contact. A tiny bolus of saline is preferably injected through the hole to replace lost aqueous humor, and the cannula tip is passed through the hole until a short length is visible in the anterior chamber. The length should be between a quarter-to-half the width of the iris to avoid cannula retraction of the eye while not interfering with vision (~1 mm for rat eyes). An opthalmic corticosteroid (triamcinolone) may be injected in lieu of saline to combat inflammatory reactions.

The cannula tip may be placed in various sections of the eye besides the anterior chamber, including the posterior chamber and vitreous chamber, as there are advantages to having a cannula implanted in these other compartments for certain applications. The procedure described in FIG. 3 is generally the same for any location.

An embodiment of the novel method may include alternative methods for securing the cannula to the eye rather than sutures. Moreover, an embodiment may include the cannula being secured to a different part of the eye rather than the sclera.

Experimental Study

Figure 4:
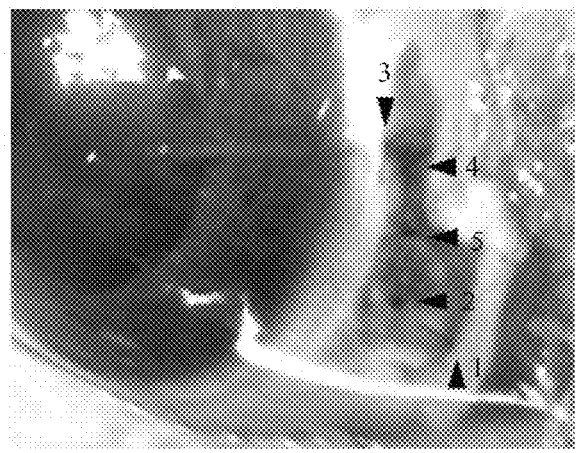
FIG. 4 is an image of an embodiment of the cannula implanted in the anterior chamber of a rat eye and secured with half-thickness sutures (arrowheads) to the sclera. Numbers indicate order of suture placement.

The feasibility of long-term implantation of a cannula in the anterior chamber was examined in twenty rats using the specifically shaped cannula of the present invention. The key to success was the fabrication of a custom mold that shaped the tip to the curvature of rat eyes and angled it into the iridocornealspace. The mold was created by bending a 23G needle into a three-dimensional figure Z. The cannula was threaded through the curved needle and permanently re-shaped by apply heat to the needle with a cautery pen. Animals were anesthetized on the day of implantation with the ketamine-xylazine mixture, supplemented as needed. The head was secured in a stereotaxic, eyes were instilled with mydriatic (1% cyclopentolate hydrochloride), and one eyelid was retracted. A 2-mm incision was made in the conjunctiva parallel to the limbus near the nasal canthus, and conjunctival tissue was dissected anteriorly to make space for cannula attachment to the sclera. The cannula was filled with artificial aqueous humor and fed into a 23G needle, which was slid through the incision to the medial orbital wall and redirected vertically to exit the scalp. The needle was removed, the cannula was cut (length: 20 mm), buried under the skin, and the Z-shaped end was anchored with 2-3 half-thickness scleral sutures. A hole was tunneled into the anterior chamber with a 33G needle that was directed under the circumlimbal venous plexus and angled to avoid iris contact. The cannula tip was passed through the hole until a short length (~1 mm) was visible in the eye (FIG. 4A). The tip was anchored with two additional half-thickness scleral sutures, the conjunctiva was closed with sutures, and the eyelid was released.

Throughout the procedure corneas were kept moist with ophthalmic solution. Every twelve hours for three days after surgery, animals were given carprofen (5 mg/kg, IM) for pain relief, and each eye was instilled with 1% cyclopentolate to prevent iris attachment and 1% prednisone to combat inflammatory processes. The cannula was implanted in the right eye, the left eye served as a control. The objective was to develop an implantation procedure that can last for weeks without permanently deflating or damaging the eye. In initial experiments, Seidel tests were conducted during the first post-operative month to check for aqueous leakage. The tests were done by touching a fluorescein strip to the cornea and observing dye clearance at the implant site with an ophthalmoscope.

Initially, the cannula was run straight from the scalp into the anterior chamber, but this approach usually failed during the first post-surgical week because of cannula migration into or out of the eye. An implantation procedure was thereby devised in which the cannula was pre-shaped to run from the scalp to the nasal canthus and around the limbus before entering the eye. Cannulas were implanted in twenty rat eyes using this procedure with a success rate of 80%. An implant was deemed a success if it remained in place for more than two weeks without causing intraocular inflammation, infection, or injury.

Figure 5:
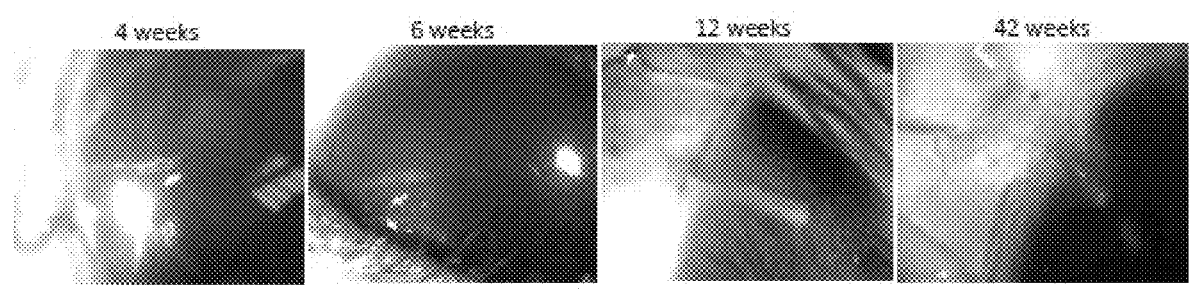
FIG. 5 is a collection of chronologically captured images of rat eyes with permanently implanted cannulas.

FIG. 5 shows pictures of rat eyes that were implanted for several months. It can be seen that the aqueous humor is clear, the cornea and iris are undamaged, and the cannula position is unchanged although the eye could freely blink and rotate. The wound healed over the cannula, and the tip shows little-to-no fibrosis. The cornea of some animals exhibited slight opacification and blood vessel growth from contact with the tip (asterisk) while the rest of the eye looked normal. No leakage of aqueous humor was detected at the implant site based on Seidel's tests performed during the first post-operative month. Moreover, Corneal curvature was largely undistorted as tip pre-shaping helped to blunt contact stresses that could cause corneal ulceration.

It can be seen that vitreous humor is clear and retinal vasculature and optic nerve striation patterns exhibit no abnormalities. Implanted eyes were processed histologically for signs of tissue inflammation and damage. The parallel layering of corneal stroma fibrils was undisturbed except by the limbus where some tortuosity and inflammatory reaction is present at the insertion site. A thin outgrowth of scar tissue was seen between the cannula and corneal endothelium, which extended toward the tip. The outgrowth was inconspicuous under direct ophthalmoscopy. The lumen and inner wall of the cannula were devoid of cellular matter. No abnormality was noted in retinal layer thickness or cell density. By all visual indications, implanted rat eyes were healthy and had accepted the cannula for life.

Physiological Evaluation of Implanted Eyes

The intraocular pressure (TOP) of implanted eyes was regularly monitored with a tonometer. FIGS. 6A and 6B shows bilateral TOP records from two rats. Readings from the implanted eye were stable over several weeks and deviated any given day by less than 3 mmHg from the nonimplanted eye. As a result, mean TOP was not significantly different between the eyes of these and all other animals examined (n=8, TOP implant=19.5±3.3 mmHg, TOP control=20.0±3.2 mmHg). The data demonstrates that cannula implantation did not cause chronic aqueous leakage or a foreign body response that alters aqueous humor production or outflow facility. Retinal health of implanted eyes was assessed with ERG recordings. FIGS. 6C and 6D show full-field ERG signals recorded from two anesthetized rats for flashes of one or more intensity presented under dark adapted conditions. Both the implanted and non-implanted eyes generated a- and b-waves of similar amplitude and time course. ERG records were collected 1-2 months after implantation from a group of rats (n=4), and the relative a- and b-wave amplitudes and implicit times of both eyes were compared. No significant difference in any of these parameters was noted (difference in a-wave amplitude: 1±7 µV, p=0.767, b-wave amplitude: 5±11 µV, p=0.539, a-wave implicit time: 0.7±2.4 ms, p=0.779, b-wave implicit time: 3.1±6.2 ms, p=0.595). The data lend further support that the retina was not injured directly by the implantation procedure or indirectly by tissue responses to the ocular implant.

The study proved that cannulas can be successfully implanted in the anterior chamber of eyes, as small as those of a rat, using the novel device and method. None of the cannulas implanted in the study slipped out or caused damage to internal tissues, even though the eye can blink and freely rotate in its socket.

Glossary of Claim Terms

Concave: means curved.

Convex: means curved in a direction distinct from that of a concave curve.

Curve: is a form that is not linear. It is also referred to herein as a bend or arc.

Medical Device: is any device used in medical and/or surgical treatments and/or the science of medicine and/or surgery.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A cannula, comprising:
    a first end and a second end with a body extending therebetween,
    the body being hollow with a first opening at the first end of the cannula and a second opening at the second end of the cannula to permit fluid to flow into and out of the body of the cannula;
    in moving from the first end of the cannula to the second end of the cannula, the body having a first curve proximate the first end of the cannula followed by a second curve, wherein the first curve is concave and the second curve is convex, the first and second curves residing generally in a first plane, wherein the first plane, when viewed along the edge of the first plane, is arced in a direction perpendicular to the edge of the first plane to a degree that roughly matches the degree of curvature of an outer surface of an eye on which the cannula is intended to be attached; and
    an insertion section disposed between the first curve of the body and the first end of the cannula, the insertion section is an elongated tubular section that is angled with respect to the first plane, such that the insertion section is not co-planar with respect to the first place, and is shaped to match a curvature of an iridocorneal angle.

2. The cannula of claim 1, further comprising the first and second curves in the body collectively appearing to be generally Z-shaped.

3. The cannula of claim 1, further comprising the first curve and the second curve having an angle less than 90-degrees.

4. The cannula of claim 1, further comprising the second end tethered to a medical device.

5. The cannula of claim 1, further including being comprised entirely of a biocompatible material.

6. A method of implanting a cannula into an eye, comprising: pre-shaping a cannula having a first end opposite a second end to include two consecutive bends separated by an intermediate section, wherein the two consecutive bends comprise a first bend and a second bend, wherein the first bend opens in a first direction and the second bend opens in a second direction, such that a shape of the two consecutive bends and the intermediate section is representative of a Z-shape; curving an attachment portion of the cannula, which includes the first bend, the intermediate section, and the second bend, to roughly match a degree of curvature of an outer surface of a subject's eye, wherein the curvature of the attachment portion of the cannula resides generally in a plane which, when viewed along the edge of the plane, is arced in a direction perpendicular to the edge of the plane to a degree that roughly matches the degree of curvature of the outer surface of the subject's eye; shaping an elongated tubular insertion section proximate to the first end to match a curvature of an iridocorneal angle of the subject's eye, wherein the insertion section is angled with respect to the plane in which the attachment portion of the cannula resides, such that the insertion section is not co-planar with the plane; cutting an incision in the subject's eye; threading the insertion section of the cannula at the first end of the cannula into the subject's eye through the incision; securing the cannula to the subject's eye by suturing at least the first bend, the intermediate section, and the second bend to the outer surface of the subject's eye; and connecting the second end of the cannula to a medical device.

7. The method of claim 6, wherein the step of pre-shaping the cannula further comprises shaping the first bend and the second bend such that each has an angle less than 90-degrees.

8. The method of claim 6, further comprising the step of dissecting conjunctival tissue to provide surgical space for attaching the cannula to the sclera in the subject's eye.

9. The method of claim 6, further comprising the step of connecting the cannula to a subdermal coupler that is anchored to bone.

10. A cannula, comprising: a first end and a second end with a body extending therebetween, the body being hollow with a first opening at the first end of the cannula and a second opening at the second end of the cannula to permit fluid to flow into and out of the body of the cannula; and in moving from the first end of the cannula to the second end of the cannula, the body having a first curve proximate the first end of the cannula followed an intermediate section and then a second curve, wherein the first curve is concave and the second curve is convex; the first curve and the second curve having an angle less than 90-degrees; the first curve, the intermediate section, and the second curve collectively residing generally in a longitudinal plane, wherein said plane is curved in a lateral direction such that when viewed along the edge of the plane, the first curve, the intermediate section, and the second curve are collectively arced to a degree that roughly matches the degree of curvature of an outer surface of an eye on which the cannula is intended to be attached; and an insertion section disposed between the first curve of the body and the first end of the cannula, the insertion section is an elongated tubular section that is angled with respect to the plane such that the insertion section is not co-planar with the plane and is shaped to match a curvature of an iridocorneal angle.

11. The cannula of claim 10, further comprising the first and second curves in the body collectively appearing to be generally Z-shaped.

12. The cannula of claim 10, further comprising the second end tethered to a medical device.

13. The cannula of claim 10, further including being comprised entirely of a biocompatible material.

\* \* \* \* \*